(12) United States Patent
Richer

(10) Patent No.: US 7,928,394 B1
(45) Date of Patent: Apr. 19, 2011

(54) TESTING DEVICE CONTAINING A GAS SENSOR

(75) Inventor: Paul A. Richer, Everett, WA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 11/842,880

(22) Filed: Aug. 21, 2007

(51) Int. Cl.
*G01N 21/35* (2006.01)

(52) U.S. Cl. ........................................................ 250/343

(58) Field of Classification Search ................... 250/343
See application file for complete search history.

(56) References Cited

U.S. PATENT DOCUMENTS

| | | | |
|---|---|---|---|
| 3,861,809 A * | 1/1975 | Hall, Jr. ........................ 356/418 |
| 4,996,431 A * | 2/1991 | Bonne et al. .................. 250/343 |
| 5,091,649 A * | 2/1992 | Rantala ......................... 250/343 |
| 5,150,360 A | 9/1992 | Perlman et al. |
| 5,207,087 A * | 5/1993 | Costello ......................... 73/1.02 |
| 5,441,076 A * | 8/1995 | Moriya et al. ................. 137/486 |
| 6,032,194 A | 2/2000 | Gai et al. |
| 6,186,177 B1 * | 2/2001 | Maher ............................ 137/884 |
| 6,388,995 B1 | 5/2002 | Gai et al. |
| 6,400,681 B1 | 6/2002 | Bertin et al. |
| 6,450,012 B1 * | 9/2002 | Mayer et al. ................... 73/49.3 |
| 6,454,923 B1 * | 9/2002 | Dodgson et al. .............. 204/415 |
| 6,535,491 B2 | 3/2003 | Gai et al. |
| 6,697,339 B1 | 2/2004 | Jain |
| 6,882,630 B1 | 4/2005 | Seaman |
| 6,976,088 B1 | 12/2005 | Gai et al. |
| 7,178,381 B2 * | 2/2007 | Tajima et al. ................. 73/31.02 |
| 7,186,979 B1 * | 3/2007 | Wong .......................... 250/336.1 |
| 7,428,658 B2 | 9/2008 | Nagin et al. |
| 2001/0056503 A1 | 12/2001 | Hibbard |
| 2002/0181503 A1 | 12/2002 | Montgomery, Jr. |
| 2003/0052792 A1 * | 3/2003 | Koyano et al. ................ 340/632 |
| 2005/0170520 A1 * | 8/2005 | Schur et al. ................... 436/149 |
| 2007/0207591 A1 | 9/2007 | Rahman et al. |
| 2007/0267568 A1 * | 11/2007 | Wolleswinkel ............ 250/214.1 |

OTHER PUBLICATIONS

U.S. Appl. No. 11/559,845, filed Nov. 14, 2006.
US Office Action dated Feb. 9, 2009 issued in U.S. Appl. No. 11/559,845.
US Office Action dated Aug. 21, 2009 issued in U.S. Appl. No. 11/559,845.
Author Unknown, NCTIS Working Draft, ANSI, Fibre Channel Switch Fabric No. 3, Revision 6.3, Feb. 19, 2003.

\* cited by examiner

*Primary Examiner* — David P Porta
*Assistant Examiner* — Djura Malevic
(74) *Attorney, Agent, or Firm* — Christensen O'Connor Johnson Kindness PLLC

(57) ABSTRACT

A testing device generally includes a housing having an inner cavity and at least first and second housing passageways extending from an environment outside the housing to the inner cavity. The testing device further includes a gas sensor contained within the inner cavity of the housing, the gas sensor having a measurement chamber and at least first and second sensor passageways. The first and second sensor passageways are fluidly connected with the first and second housing passageways in a hermetically sealed manner to prevent the passage of fluids from the inner cavity of the housing to the measurement chamber of the gas sensor.

18 Claims, 5 Drawing Sheets

TESTING DEVICE CONTAINING A GAS SENSOR

TECHNICAL FIELD

The present disclosure relates generally to testing devices, and more particularly, to testing devices containing gas sensors, such as infrared gas sensors.

BACKGROUND

Current gas sensors, such as carbon dioxide sensors that detect carbon dioxide content or concentration in a sample of air, are generally contained in sensor housings, for example, housings that are attachable to a wall in a testing environment. Air flows from the testing environment freely through passages into and out of the housing for testing by the sensor.

While these gas sensors are sufficient for use as stationary testing devices, these current devices do not allow for rapid and accurate gas testing when a testing environment changes abruptly, for example, when entering a room using a portable testing device, such as a hand-held device. In that regard, gas exchange within current housing designs is delayed by the volume of the housing and the limitations on gas flow rate into and out of the housing. Therefore, there exits a need for a testing device with improved diffusion for complete gas exchange within the testing device for rapid and accurate testing.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a testing device is provided. The testing device generally includes a housing having an inner cavity and at least first and second housing passageways extending from an environment outside the housing to the inner cavity. The testing device further includes a gas sensor contained within the inner cavity of the housing, the gas sensor having a measurement chamber and at least first and second sensor passageways. The first and second sensor passageways are fluidly connected with the first and second housing passageways in a hermetically sealed manner to prevent the passage of fluids from the inner cavity of the housing to the measurement chamber of the gas sensor.

In accordance with another embodiment of the present disclosure, a testing device is provided. The testing device generally includes a housing having an inner cavity. The testing device further includes a gas sensor disposed within the inner cavity of the housing, the gas sensor having a measurement chamber and at least first and second sensor passageways. The first and second sensor passageways are fluidly connected with an environment exterior to the housing, but hermetically isolated from the inner cavity.

In accordance with another embodiment of the present disclosure, a portable testing device is provided. The portable testing device generally includes a housing sized and configured to be carried in a single hand of a user, the housing having an inner cavity and at least first and second housing passageways from an environment outside the housing to the inner cavity. The portable testing device further includes a gas sensor contained within the inner cavity of the housing, the gas sensor having a measurement chamber and at least first and second sensor passageways. The first and second sensor passageways are fluidly connected with the first and second housing passageways in a hermetically sealed manner to prevent the passage of fluids from the inner cavity of the housing to the measurement chamber of the gas sensor. The gas sensor outputs signals indicative of gas content or concentration of a gas sample located within the measurement chamber. The portable testing device further includes an output device for outputting to a user the gas content or concentration of the gas sample

DESCRIPTION OF THE DRAWINGS

The foregoing aspects and many of the attendant advantages of this disclosure will become more readily appreciated by reference to the following detailed description, when taken in conjunction with the accompanying drawings, wherein.

DETAILED DESCRIPTION

Figure 1:
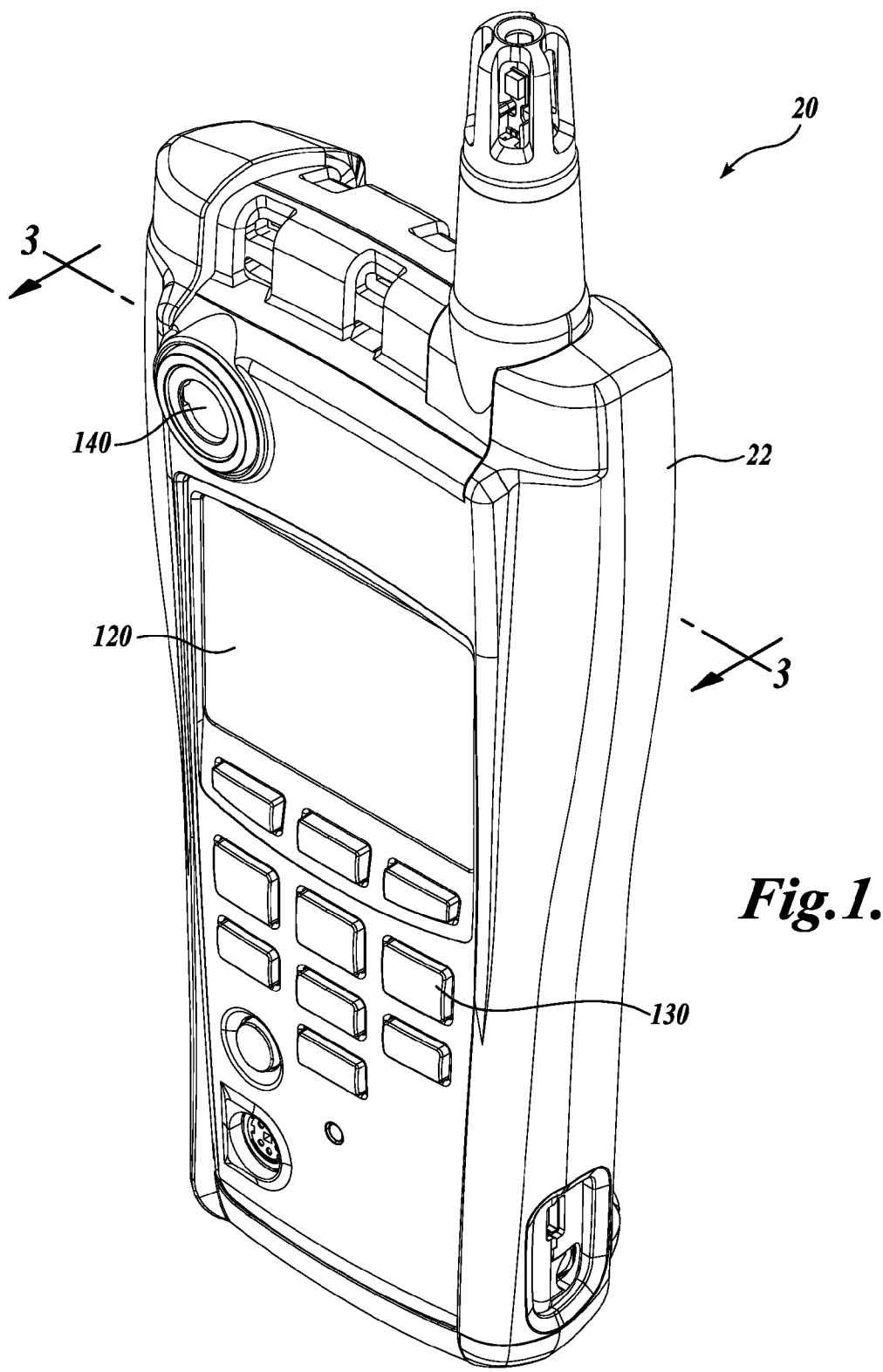
FIG. 1 is a perspective front view of a testing device in accordance with one embodiment of the present disclosure.
Figure 2:
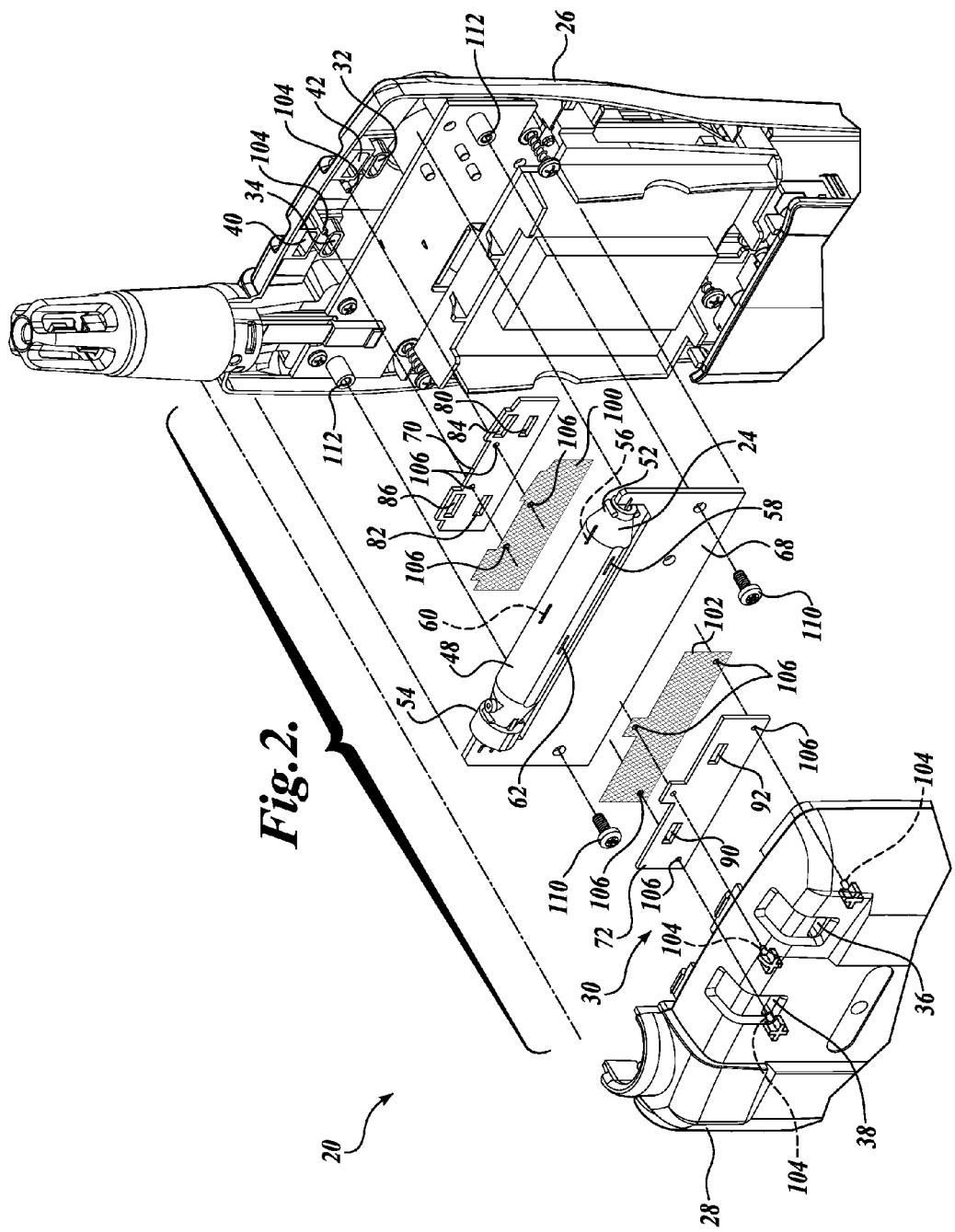
FIG. 2 is a partial exploded view of the testing device of FIG. 1.
Figure 3:
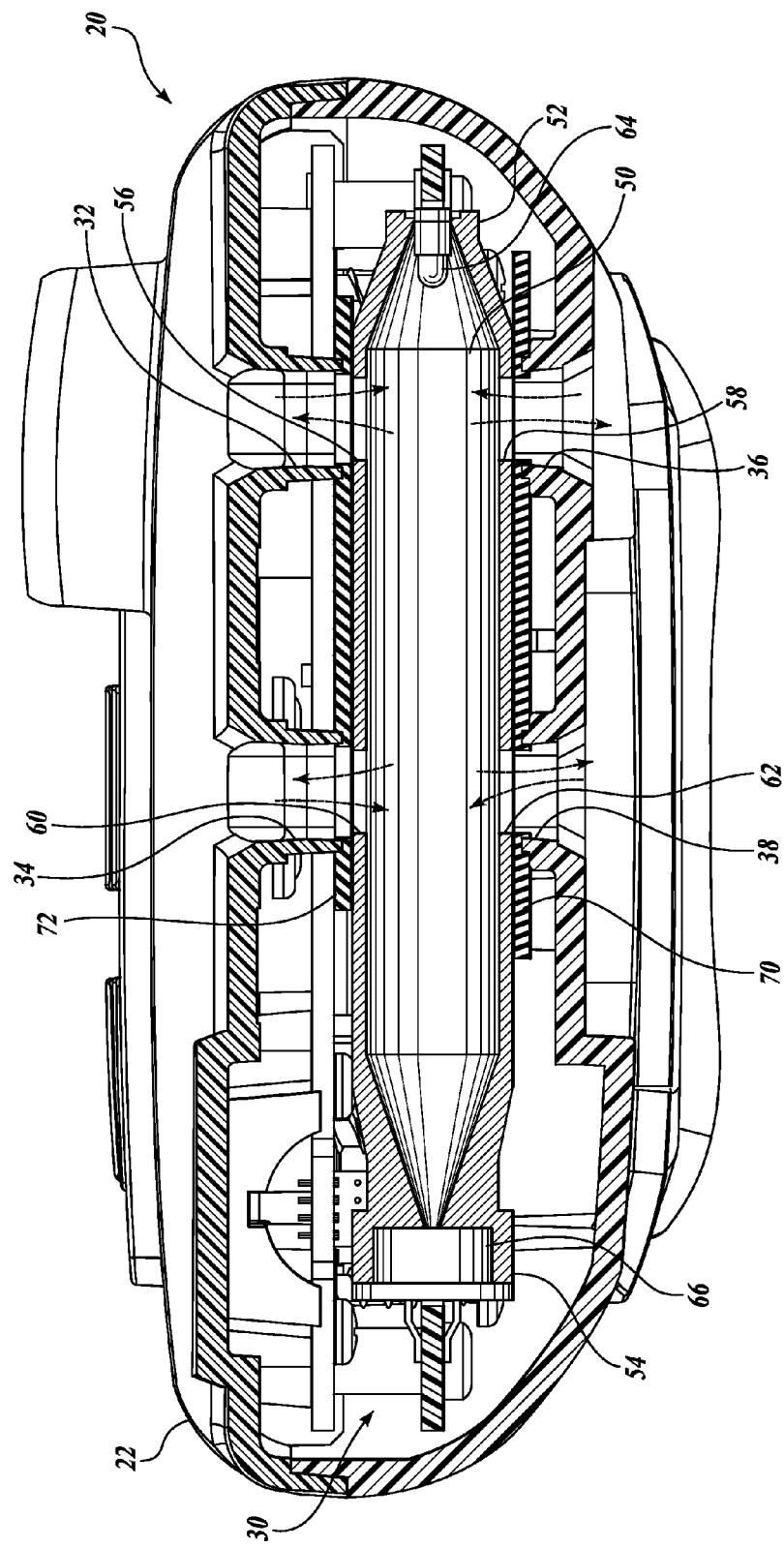
FIG. 3 is a cross-sectional view of the testing device taken through plane 3-3 shown in FIG. 1.

Embodiments of the present disclosure are generally directed to testing devices having gas sensors. Referring to FIGS. 1-3, there is shown a testing device, generally indicated 20, constructed in accordance with the one embodiment of the present disclosure. The device 20 generally includes a housing 22 and a gas sensor 24 disposed within the housing 22 (see FIG. 2). As will be described in detail below, the housing 22 and the gas sensor 24 are cooperatively configured and arranged to provide rapid and accurate detection of the content or concentration of a component of ambient gas, which allows embodiments of the device 20 to be suitably used for testing applications requiring portability.

In the embodiments shown, the device 20 is of the portable type. In that regard the device 20 may be sized and configured to be portable, as a non-limiting example, to be carried in a single hand of a user. However, it should be appreciated that non-portable or stationary testing devices are also within the scope of the present disclosure. For a more detailed description of other aspects of the portable testing device 20, please see co-pending U.S. patent application Ser. No. 11/842,885, now U.S. Pat. No. 7,802,472; U.S. patent application Ser. No. 11/842,893; and U.S. Design Pat. No. D571,680, all filed on Aug. 21, 2007, the disclosures of which are hereby incorporated by reference.

Turning now to FIG. 2, the testing device 20 will be described in greater detail. As best seen in FIG. 2, the housing 22 includes a plurality of passageways extending from an environment exterior to the housing 22 to the inner cavity 30 of the housing 22 and vice versa. In the illustrated embodiment, such a plurality of passageways are first, second, third, and fourth passageways 32, 34, 36, and 38. It should be appreciated that while four housing passageways are shown in the illustrated embodiment, any number of housing passageways are within the scope of the present disclosure, so long as at least some of the housing passageways are designed to be fluidly connected with the gas sensor 24, as described in greater detail below. As a non-limiting example, housing passageways 40 and 42 provide ventilation and pressure equalization for the inner cavity 30 of the housing 22, but are not configured to be fluidly connected with the gas sensor 24.

As best seen in FIG. 2, the housing 22 is made up of first and second casings 26 and 28, such that when joined together, the casings 26 and 28 define the inner cavity 30. The casings 26 and 28, respectively, define the front and back portions of the device 20. It should be appreciated that the casings 26 and 28 may be joined together by any suitable coupling means, such as a snap fit connection, a fastening system, such as screws, or any other coupling devices, adhesive, and various welding techniques, including plastics heat welding, ultrasonic welding, vibration welding, etc. It should further be appreciated that other housing designs besides front and back casings that define an inner cavity are also within the scope of the present disclosure.

As seen in the illustrated embodiment of FIGS. 1-3, the housing passageways 32, 34, 36, and 38 are preferably positioned in the upper portion of the housing 22. However, it should be appreciated that the housing passageways may be suitably positioned anywhere in the housing 22, so long as at least some of the housing passageways are designed to be fluidly connected with the gas sensor 24, as mentioned above and described in greater detail below. The housing passageways are designed and configured to be open, unobstructed passageways to the gas sensor 24 while providing minimal distance between the environment exterior to the device 20 and the gas sensor 24 disposed within the inner cavity 30 of the housing 22, such that efficient gas exchange within the gas sensor 24 is achieved. In that regard and as best seen in FIG. 3, the spacing between housing passageways 32 and 36 and housing passageways 34 and 38 (i.e., the width of the inner cavity 30 of the housing 22) at the upper portion of the housing 22 is sized and configured to substantially correspond with the diameter of the gas sensor 24.

Turning now to FIGS. 2 and 3, the gas sensor 24 is disposed within the inner cavity 30 of the housing 22 and receives a quantity of ambient gas ("ambient gas sample") from exterior the housing through housing passageways 32, 34, 36, and 38, as well as sensor passageways, described below. The gas sensor 24 is configured to measure gas component content or concentration in the ambient gas sample, for example, carbon dioxide content or concentration in a sample of air. The gas sensor 24 is further configured to generate appropriate output signals that are indicative of the gas component content or concentration present in the ambient gas sample. The gas sensor 24 preferably uses infrared absorption spectroscopy techniques to measure the gas component content or concentration and outputs appropriate output signals indicative thereof. However, it will be appreciated that embodiments of the gas sensor 24 may use other spectroscopy techniques, such as Raman scattering or photoacoustic spectroscopy, and therefore, these techniques are also within the scope of the present disclosure.

As will be described in more detail below, the output signals generated by the gas sensor 24 are transmitted to appropriate system circuitry for processing, for example, to determine the presence, content, or concentration of one or more gases in an ambient gas sample. The processed signals may then be outputted to the user in an appropriate manner, for example, displayed on an associated display.

A gas sensor 24 constructed in accordance with one embodiment of the present disclosure will now be described in more detail. As best seen in FIG. 2, the gas sensor 24 generally includes a sensor body 48 that defines a measurement chamber 50 of known length. The sensor body 48 includes first and second ends 52 and 54 and a plurality of passageways extending from an environment exterior to the sensor 24 to the measurement chamber 50 of the sensor 24 and vice versa. The passageways are designed and configured to allow for efficient diffusion or pumping of ambient gas, such as air, into the sensor measurement chamber 50. In the illustrated embodiment, the sensor 24 includes first and second passageways 56 and 58 disposed near the first end 52 and third and fourth passageways 60 and 62 disposed near the second end 54. However, like the housing passageways, it should be appreciated that any number of sensor passageways are within the scope of the present invention, so long as all of the sensor passageways are designed to be fluidly connected with housing passageways to prevent gases trapped within the housing inner cavity 30 from entering the sensor passageways, as described in greater detail below.

The gas sensor 24 further includes an emitter 64 mounted at the first end 52 and a detector 66 mounted at the second end 54. In addition, the gas sensor 24 includes a circuitry plate 68, to which the sensor body 48 is coupled both electrically and structurally.

In one embodiment, the emitter 64 is configured to emit infrared light either in a dispersive or non-dispersive manner in the direction of the detector 66 through the chamber 50. In this embodiment, the detector 66 is configured to detect the intensity of the emitted light that reaches the detector and to generate electrical output signals representative thereof. In embodiments that utilize non-dispersive emitters, such as incandescent light bulbs, it will be appreciated that filters disposed in front of the detector 66 are typically used for selecting the wavelength associated with the type of gas to be measured, for example, carbon dioxide.

One non-limiting example of a non-dispersive infrared (NDIR) that may be practiced with embodiments of the present disclosure is a silicon-based single-beam dual-wavelength NDIR sensor manufactured under the trademark CARBOCAP® by Vaisala. Such a NDIR sensor is typically configured to detect carbon dioxide; however, it should be appreciated that the gas sensor can be configured to measure other discrete gas components, including, but not limited to, methane, sulfur dioxide, nitric oxide, and carbon monoxide.

Alternatively, the emitter 64 may be configured to emit laser light in either the visible, near infrared, or near ultraviolet range in the direction of the detector 66 through the chamber 50. In this embodiment, the detector 66 is configured to measure the amount of light that the ambient gas sample scatters and generates electrical output signals representative thereof. The detector 66 in this embodiment may be a photon-counting photomultiplier tube (PMT) or a charge-coupled device or camera. Other conventional components utilized in conventional Raman-type scattering spectroscopy techniques may be used, such as wavelength filters (e.g., monochromators, etc.)

Referring to FIG. 3, the sensor passageways are fluidly connected to the housing passageways to allow for efficient diffusion or pumping of a gas sample into the sensor measurement chamber 50. In that regard, housing passageways 32, 34, 36, and 38 are aligned with respective sensor passageways 56, 60, 58 and 62. When the housing and sensor passageways are aligned, ambient gas flows directly from the environment outside the device 20 into the sensor measurement chamber 50, rather than traveling into the remaining volume of the housing inner cavity 30 before entering the sensor measurement chamber 50. The alignment of the housing and sensor passageways further prevents gases trapped within the housing inner cavity 30, which may not have not been exchanged and therefore may not be indicative of present ambient conditions, from traveling from the housing inner cavity 30 to the sensor measurement chamber 50, as typically allowed in previously designed devices.

The housing and sensor passageways are connected in a hermetically sealed manner to further prevent the passage of fluids from the inner cavity 30 of the housing 22 to the measurement chamber 50 of the gas sensor 24. In the illustrated embodiment of FIG. 2, first and second gaskets 70 and 72 adjoin the sensor 24 between the sensor 24 and the first and second casings 26 and 28 of the housing 22. The gaskets 70 and 72 are designed and configured to provide a seal between the housing and sensor passageways to prevent the leakage of any gases and preferably are made from any suitable elastomeric material. In that regard, the first gasket 70 includes cut out portions 80 and 82 that align with and seal the housing passageways 32 and 34, respectively, and the sensor passageways 56 and 60, respectively. In the illustrated embodiment, the first gasket 70 further includes additional cut out portions 84 and 86 that align with the housing passageways 40 and 42 that provide ventilation and pressure equalization for the inner cavity 30 of the housing 22, as described above. The second gasket 72 includes cut out portions 90 and 92 that align with and seal the housing passageways 36 and 38, respectively, and the sensor passageways 58 and 62, respectively.

The gaskets 70 and 72 are preferably designed not only to provide a passageway sealing function, but also to prevent moisture, dirt, debris, and other contaminants from entering either the inner cavity 30 of the housing 22 to the measurement chamber 50 of the gas sensor 24. In that regard, the gaskets 70 and 72 are preferably hydrophobic gaskets. The gaskets 70 and 72 further may include first and second filters 100 and 102, to prevent dust and debris from entering the housing 22 or the sensor measurement chamber 50. Therefore, suitable filters are designed and configured to allow the passage of gases, but not the passage of dirt or debris. In that regard, the filters are preferably within a mesh range of about 25 μm to about 125 μm, and preferably about 40 μm.

Still referring to FIG. 2, the gaskets 70 and 72 (including filters 100 and 102) are maintained in alignment with the housing and sensor passageways by coupling with an inner surface of the first and second casings 26 and 28 in proximity to the housing passageways and/or to an outer surface of the sensor measurement chamber 50 in proximity to the sensor passageways. In the illustrated embodiment, the inner cavity of the first casing 26 includes a plurality of protrusions 104 extending inwardly that are design and configured to cooperatively engage with a plurality of protrusion receiving holes 106 in the first gasket 70 and first filter 100. Likewise, the inner cavity of the second casing 28 includes a plurality of protrusions 104 extending inwardly that are designed and configured to cooperatively engage with a plurality of protrusion receiving holes 106 in the second gasket 72 and second filter 102. It should be appreciated, however, that other means of coupling the gaskets 70 and 72 and filters 100 and 102 to an inner surface of the first and second casings 26 and 28 and/or to an outer surface of the sensor measurement chamber 50 are within the scope of the present disclosure. As a non-limiting example, the gaskets 70 and 72 and filters 100 and 102 may be coupled by adhesive to an inner surface of the housing 22 and/or to an outer surface of the sensor measurement chamber 50.

While the seals between the housing and sensor passageways are shown as gaskets 70 and 72 in the illustrated embodiment of FIGS. 1-3, it should be appreciated that other seals besides gaskets are within the scope of the present disclosure. Additionally, other equivalent structure for providing this sealing function is also with the scope of the present disclosure and may include, but is not limited to, adhesive, sealants, such as silicon sealants, heat bonding the sensor body to the casings, etc.

In the illustrated embodiment, the gas sensor 24 is mounted in the inner cavity 30 of the housing 22 by a plurality of fasteners 110. As best seen in FIG. 2, fasteners 110, such as screws, attach the sensor circuitry plate 68 to fastener receiving holes 112 in the first casing 26. However, it should be appreciated that the gas sensor 24 may be mounted by any suitable mounting means, including adhesive, an interference fit with the inner cavity, and any other suitable mounting devices.

Returning to FIG. 1, it should be appreciated that the device 20 may include other conventional device components, such as a display 120 for displaying gas detection results associated with the sensor 24, one or more input devices 130 associated with the operation or calibration of the sensor 24, system circuitry and electronics for supplying power to the various device components, including the emitter 64 and the detector 66, and for processing the electrical output signals of the gas sensor 24, and signaling devices for outputting visual or audible warning signals in response to the processed sensor signals. The device 20 may also include other discrete and/or integrated testing components, including, but not limited to, a temperature monitor, a barometer, a carbon monoxide monitor, and other environmental and air quality monitoring devices.

The operation of the system will now be described with reference to FIG. 3, a cross-sectional view of the device 20 taken through plane 3-3 shown in FIG. 1. As mentioned above, the device 20 may be a portable (i.e., handheld) testing device that can be transported by a user or by other transport means from one environment to another, for example, from one room to another room in a building, or from an outside environment to an environment inside a building or other structure. Ambient gas constantly travels through the fluidly connected housing and sensor passageways to the measurement chamber 50 of the sensor 24 for gas component detection, as indicated by the arrows. As described above, when in use, the sensor 24 measures the gas component content or concentration in the ambient gas sample.

Because gas exchange is not required within the entire inner cavity 30 of the housing 22, but only within the measurement chamber 50 for accurate gas component sensing and detection, the device 20 provides rapid sample testing of ambient gases. In that regard, the testing device 20 generally requires less than about 30 minutes to stabilize in the case of extreme environmental condition changes, for example, a change from a 5000 ppm carbon dioxide environment to a 500 ppm carbon dioxide environment (typical reading for outside air). In other less extreme environmental condition changes, for example, a change from a 800 ppm carbon dioxide environment to a 500 ppm carbon dioxide environment, the testing device 20 generally requires less than about 5 minutes to stabilize.

As the sensor 24 reads the gas content or concentration of a specific component in an ambient gas sample, such as carbon dioxide content or concentration in air, the sensor 24 works in connection with the system circuitry and electronics that process the sensor signals and display 120 and/or other signaling devices to provide an output display and/or signal. Such outputs may include audible and/or visual signals, such as, but not limited to, audible or visible alarms, lights, or messages, and a display of the testing results.

Figure 4:
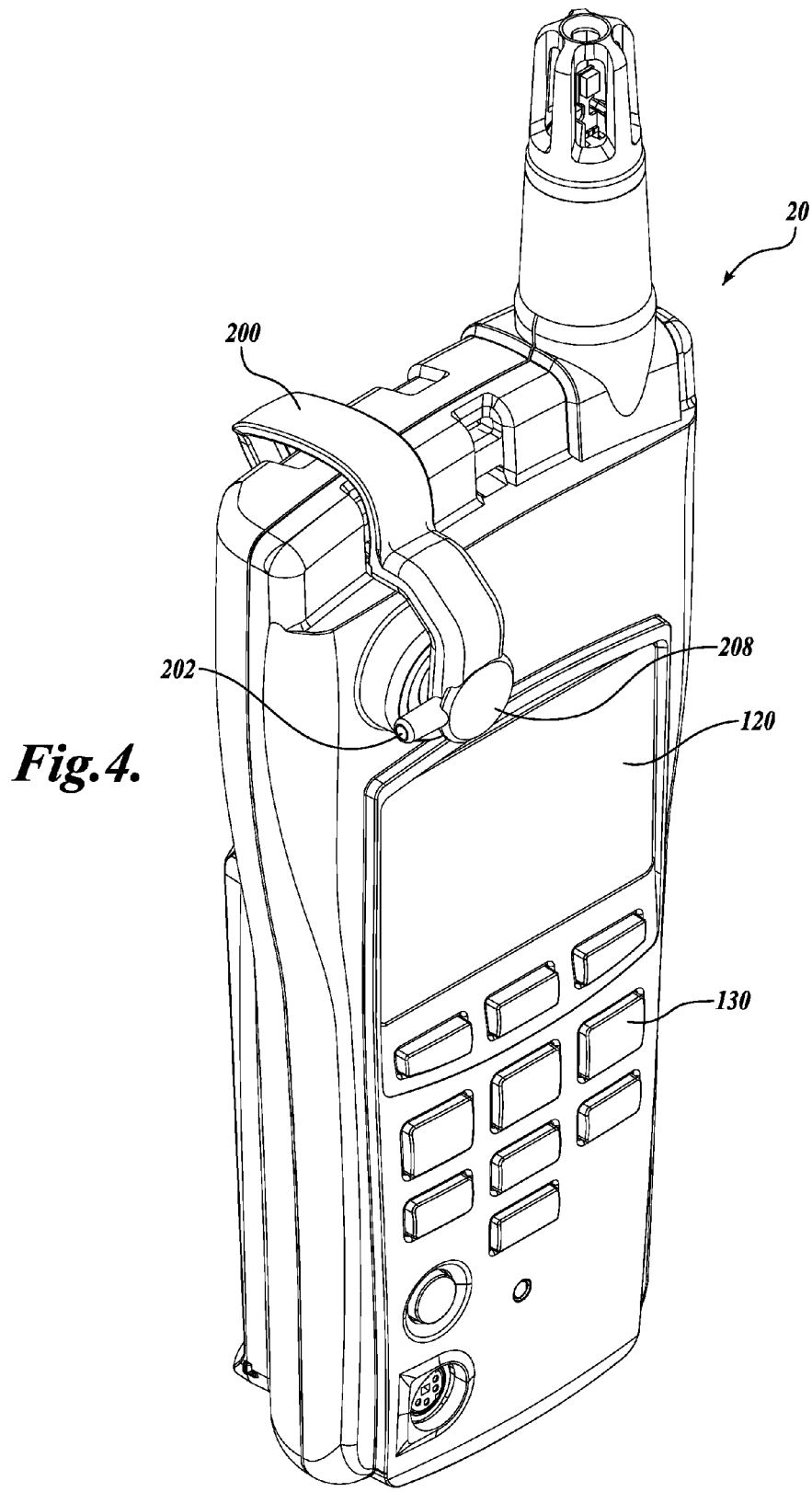
FIG. 4 is a perspective front view of the testing device of FIG. 1 having a calibrating device attached thereto.
Figure 5:
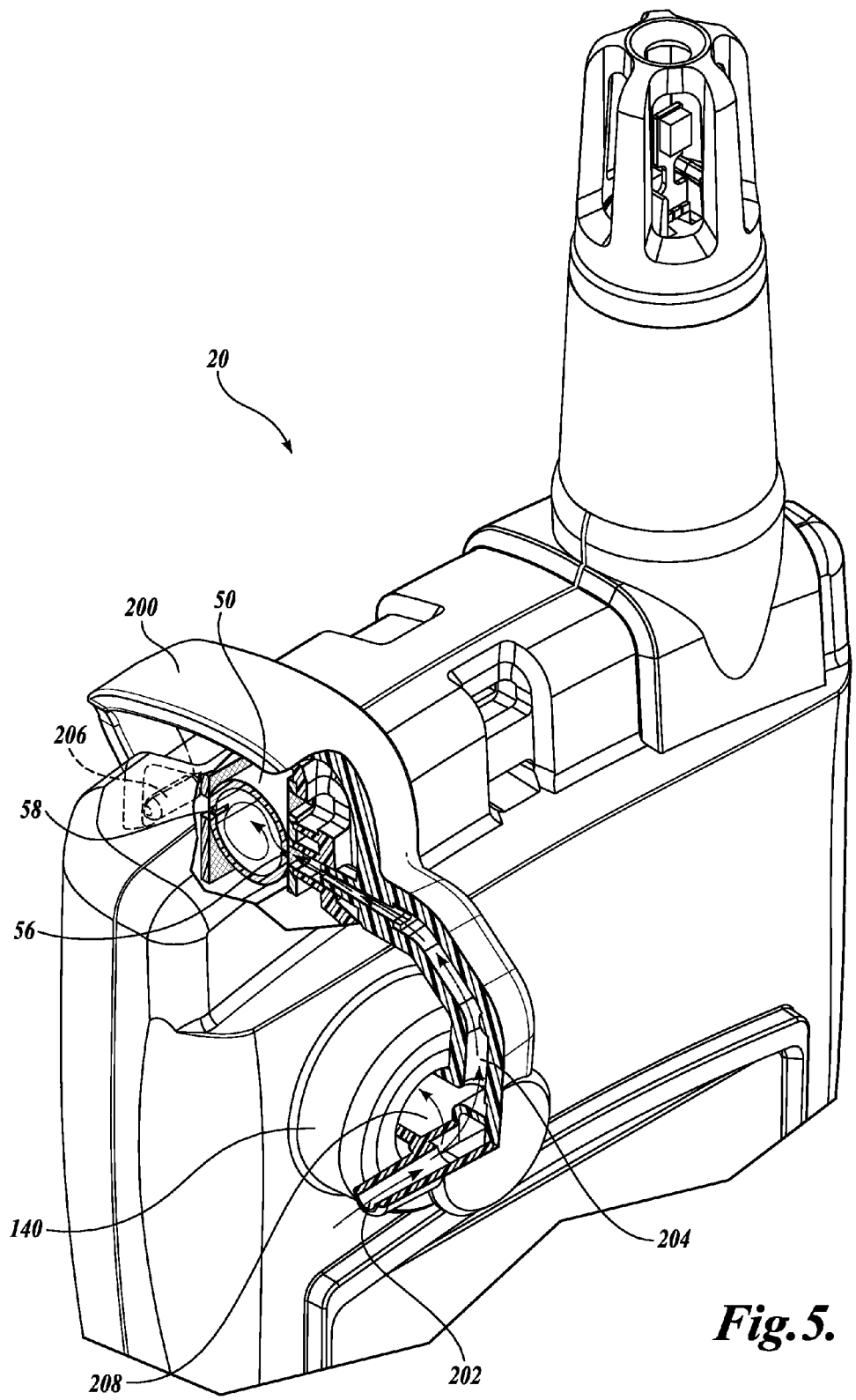
FIG. 5 is a partial cut away view of the testing device and calibrating device of FIG. 4.

Now referring to FIGS. 4 and 5, a calibration device 200 for use when calibrating the testing device 20 will be described in greater detail. The calibration device 200 is designed and configured to pump calibrating gas having a known concentration of a gas component to be detected into the sensor 24. It should be appreciated that calibrating gas is generally pumped into the calibration device 200 and the sensor measurement chamber 50 at a higher pressure than ambient air pressure to prevent ambient non-calibrating gases from simultaneously entering the sensor measurement chamber 50. As best seen in FIG. 5, the calibration device 200 includes a gas inlet 202 and a first gas channel 204 fluidly connected with at least one sensor passageway 56.

The calibration device 200 may further include a passageway plug 206 for restricting the flow of the calibration gas from the measurement chamber 50 through sensor passageway 58 located on the opposite side of the measurement channel 50 from the inlet sensor passageway 56, as best seen in FIG. 5. While the passageway plug 206 prevents calibration gas pumped into sensor passageway 56 from immediately exiting the sensor measurement chamber 50 at sensor passageway 58 and aids in speeding up the time required for sensor 24 calibration, it should be appreciated that passageway plug 206 is not required for calibration, particularly if the calibrating gas is pumped into the sensor measurement chamber 50 at a higher pressure than ambient air pressure.

In the embodiment shown, the calibration device 200 is suitably a clip having a snap fit with the top portion of housing 22 of the device 20. However, it should be appreciated that other coupling methods for the calibration device 200 are within the scope of the present disclosure.

During use, a flow of calibration gas having a known component content or concentration, for example, a known concentration of carbon dioxide, travels through the gas inlet 202 and first gas channel 204 into the sensor measurement chamber 50 at sensor passageway 56, as indicated by the arrows. As a non-limiting example of a suitable calibration procedure, 0.5 liters per minute of a gas having a known carbon dioxide concentration is pumped through the calibration device 200. Once in the sensor measurement chamber 50, the gas is forced to flow out of sensor passageways 60 and 62, due to the pressure of the calibration gas and the plugging of sensor passageway 58. The sensor 24 detects the gas component content or concentration in the calibration fluid, and if the reading does not correspond with the known component content or concentration, then calibrating adjustments can be made to the device 24, either automatically or manually by the user. In this example, the calibration time for the sensor 24 is generally less than about 1 minute.

It should further be appreciated that the calibration device 200 may be configured to calibrate other components of the testing device besides sensor 24. As a non-limiting example, in the illustrated embodiment of FIGS. 4 and 5, the gas inlet 202 is fluidly connected with a second gas channel 208 leading to a second sensor 140, such as a carbon monoxide monitor 140 located on the face of the device 20 (see FIG. 1). Therefore, the calibration device 200 of the illustrated embodiment is configured to direct calibrating gas to at least two sensors, sensor 24 and second sensor 140. Accordingly, for ease of calibration, the calibration gas formula can be designed for calibrating multiple device sensor calibrations at once, for example, the calibrating gas may contain a known quantity of carbon monoxide gas and a known quantity of carbon dioxide gas. It should be appreciated that the calibration device 200 may also include other gas channels leading to other optional components of the testing device 20 during calibration.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A testing device, comprising: (a) a housing having an inner cavity and at least first, second, third, and fourth open housing passageways extending from an environment outside the housing to the inner cavity to allow the bidirectional diffusion of gas between the environment and the housing passageways; and (b) a gas sensor contained within the inner cavity of the housing, the gas sensor having a measurement chamber further comprising an emitter and a detector in optical communication with the emitter, and at least first, second, third, and fourth open sensor passageways, wherein the sensor passageways are fluidly connected with the housing passageways in a hermetically sealed manner to allow the bidirectional diffusion of gas between the environment and the measurement chamber of the gas sensor and to prevent the passage of fluids from the inner cavity of the housing to the measurement chamber of the gas sensor.

2. The testing device of claim 1, wherein the sensor is an infrared absorption sensor.

3. The testing device of claim 1, wherein the sensor is a non-dispersive infrared sensor.

4. The testing device of claim 1, wherein the sensor detects carbon dioxide content in a sample of air.

5. The testing device of claim 1, further comprising a display for displaying the output of the gas sensor.

6. The testing device of claim 1, further comprising a signaling device.

7. A testing device, comprising: (a) a housing having an inner cavity; and (b) a gas sensor disposed within the inner cavity of the housing, the gas sensor having a measurement chamber further comprising an emitter and a detector in optical communication with the emitter, and a plurality of open sensor passageways, wherein the plurality of sensor passageways are fluidly connected with an environment exterior to the housing, but hermetically isolated from the inner cavity to prevent fluid communication between the inner cavity and a measurement chamber, wherein each of the sensor passageways is configured to permit ambient gas from the environment outside the housing to bidirectionally diffuse in and out of the measurement chamber of the gas sensor.

8. The testing device of claim 7, wherein the sensor is an infrared absorption sensor.

9. The testing device of claim 7, wherein the sensor is a non-dispersive infrared sensor.

10. The testing device of claim 7, wherein the sensor is a carbon dioxide gas sensor.

11. The testing device of claim 7, further comprising a calibrating device having a gas inlet, wherein the gas inlet is fluidly connected with at least one of the first and second sensor passageways.

12. The testing device of claim 11, wherein the calibrating device further includes a passageway plug for restricting the flow from the other of the first and second sensor passageways.

13. A portable testing device, comprising: (a) a housing sized and configured to be carried in a single hand of a user, the housing having an inner cavity and at least first, second, third, and fourth open housing passageways from an environment outside the housing to the inner cavity to allow the bidirectional diffusion of gas between the environment and the housing passageways; and (b) a gas sensor contained within the inner cavity of the housing, the gas sensor having a measurement chamber further comprising an emitter and a detector in optical communication with the emitter, and at least first, second, third, and fourth open sensor passageways, wherein the first, second, third, and fourth sensor passageways are fluidly connected with the first, second, third, and fourth open housing passageways in a hermetically sealed manner to allow the bidirectional diffusion of gas between the environment and the measurement chamber of the gas sensor and to prevent the passage of fluids from the inner cavity of the housing to the measurement chamber of the gas sensor, wherein each of the sensor passageways is configured to permit ambient gas from the environment outside the housing to diffuse in and out of the measurement chamber of the gas sensor, and wherein the gas sensor outputs signals indicative of gas content or concentration of a gas sample located within the measurement chamber; and (c) an output device for outputting to a user the gas content or concentration of the gas sample.

14. The testing device of claim 1, wherein each of the first and second sensor passageways permits gas from the environment to diffuse into the measurement chamber of the gas sensor.

15. The testing device of claim 7, wherein each of the first and second sensor passageways permits gas from the environment to diffuse into the measurement chamber of the gas sensor.

16. The testing device of claim 1, wherein the first and second sensor passageways remain open to the environment.

17. The testing device of claim 7, wherein the first and second sensor passageways remain open to the environment.

18. A method of using a portable testing device, the method including: (a) placing the testing device in a first environment having a first gas composition, the testing device including a housing having an inner cavity and a gas sensor disposed within the inner cavity of the housing, the gas sensor having a measurement chamber further comprising an emitter and a detector in optical communication with the emitter, and a plurality of open sensor passageways, wherein the plurality of open sensor passageways are fluidly connected with an environment exterior to the housing, but hermetically isolated from the inner cavity to prevent fluid communication between the inner cavity and a measurement chamber;

(b) allowing the first gas composition to bidirectionally diffuse in and out of each of the plurality of passageways until the measurement chamber is filled with the first gas composition; and (c) purging the gas sensor of the first gas composition by placing the testing device in a second environment having a second gas composition and allowing the second gas composition to bidirectionally diffuse in and out of each of the plurality of passageways until the measurement chamber is filled with the second gas composition.

* * * * *

UNITED STATES PATENT AND TRADEMARK OFFICE
CERTIFICATE OF CORRECTION

| | | |
|---|---|---|
| PATENT NO. | : 7,928,394 B1 | Page 1 of 1 |
| APPLICATION NO. | : 11/842880 | |
| DATED | : April 19, 2011 | |
| INVENTOR(S) | : P. A. Richer | |

It is certified that error appears in the above-identified patent and that said Letters Patent is hereby corrected as shown below:

| COLUMN | LINE | ERROR |
|---|---|---|
| 10 (Claim 15, | 1 line 1) | "claim 7," should read --claim 13,-- |
| 10 (Claim 17, | 7 line 1) | "claim 7," should read --claim 13,-- |

Signed and Sealed this
Sixteenth Day of August, 2011

David J. Kappos
*Director of the United States Patent and Trademark Office*